United States Patent [19]

Meilland

[11] Patent Number: Plant 6,807

[45] Date of Patent: May 23, 1989

[54] ROSE PLANT — MEIPLATIN VARIETY

[75] Inventor: Alain A. Meilland, Antibes, France

[73] Assignee: The Conard-Pyle Company, West Grove, Pa.

[21] Appl. No.: 143,613

[22] Filed: Jan. 12, 1988

[30] Foreign Application Priority Data

Jan. 13, 1987 [DE] Fed. Rep. of Germany ..... ROS590

[51] Int. Cl.[4] ..... A01H 5/00

[52] U.S. Cl. ..... Plt./1

[58] Field of Search ..... Plt. 1

*Primary Examiner*—James R. Feyrer

*Attorney, Agent, or Firm*—Burns, Doane, Swecker & Mathis

[57] ABSTRACT

A new and distinct variety of shrub rose plant is provided which forms attractive double very pale orient pink blossoms. The blossoms are formed abundantly and continuously and possess firm petals which detach cleanly. The vegetation is vigorous. The new variety is not particularly affected by crytogamic diseases, possesses decorative foliage, and is well suited for use as ornamentation in the landscape.

1 Drawing Sheet

SUMMARY OF THE INVENTION

The new variety of shrub rose plant of the present invention was created by artificial pollination wherein two parents were crossed which previously had been studied in the hope that they would contribute the desired characteristics. The female parent (i.e., the seed parent) was the product of the pollination of the Sea Foam variety (U.S. Plant Pat. No. 2,463) by the Meisecaso variety (non-patented). The male parent (i.e., the pollen parent) of the new variety was the Sea Foam variety. The parentage of the new variety can be summarized as follows:

[Sea Foam × Meisecaso] × Sea Foam.

The seeds resulting from the above pollination were sown and 22 plantlets were obtained which were physically and biologically different from each other. Selective study resulted in the identification of a single plant of the new variety.

It is found that the new variety of shrub rose plant possesses the following combination of characteristics:

(a) forms attractive double blossoms which are very pale orient pink in coloration;
(b) forms petals which are firm and drop off cleanly,
(c) forms attractive glossy foliage,
(d) exhibits a low semi-prostrate growth habit,
(e) exhibits good disease resistance, and
(f) is particularly well suited for growing in the landscape.

The new variety meets the needs of the horticultural industry for all uses. It can be grown to advantage as an attractive ornamentation in parks, gardens, public areas, and residential landscapes.

The characteristics of the new variety have been found to be homogeneous and stable and are strictly transmissible by asexual propagation (e.g., by budding, grafting, cuttage, etc.) from one generation to another.

The new variety has been named the Meiplatin variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were three years of age and grown on their own roots in the open air at Cannet-des-Maures, Var, France while observed in September.

DETAILED DESCRIPTION

Figures 1, 2, 3, 4, 5, 6, 7, 8, 9, 10, 11, 12, 13, 14, 15, 16, 17:
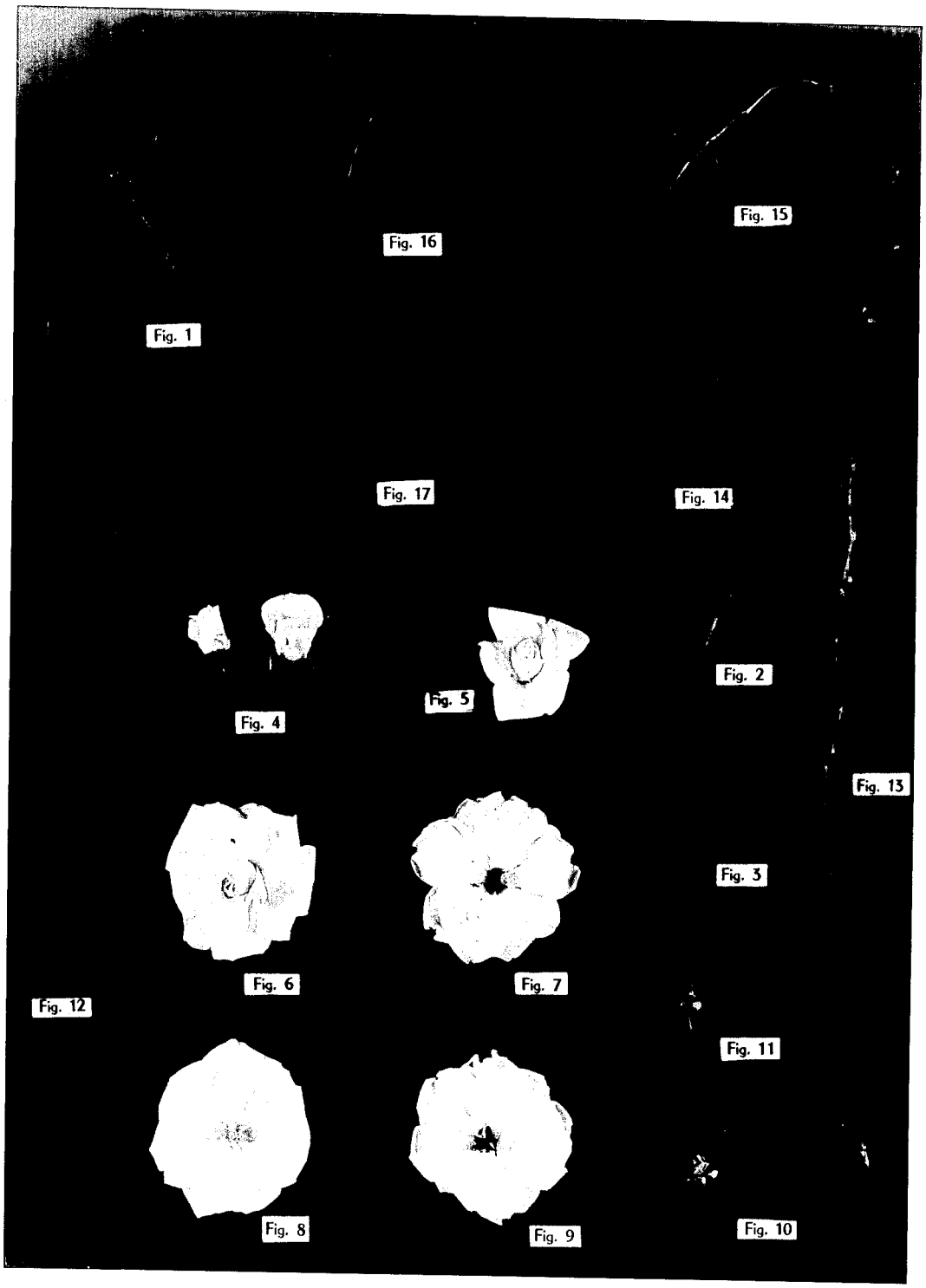
FIG. 1 illustrates a specimen of a young shoot.
FIG. 2 illustrates a specimen of two floral buds before the opening of the sepals.
FIG. 3 illustrates a specimen of two floral buds as the sepals open.
FIG. 4 illustrates a specimen of two floral buds as the petals open.
FIG. 5 illustrates a specimen of a flower in the course of blooming.
FIG. 6 illustrates a specimen of a open flower — plan view — obverse.
FIG. 7 illustrates a specimen of a open flower — plan view — reverse.
FIG. 8 illustrates a specimen of a open flower immediately prior to petal drop — plan view — obverse.
FIG. 9 illustrates a specimen of a open flower immediately prior to petal drop — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets — upper and under surfaces.
FIG. 15 illustrates specimens of leaves with five leaflets — upper and under surfaces.
FIG. 16 illustrates specimens of leaves with seven leaflets — plan view — upper and under surfaces.
FIG. 17 illustrates specimens of three fruits.

The chart used in the identification of the colors is that of The Royal Horticultural Society (R.H.S. Colour Chart). The terminology preceding the numbered reference has been added to indicate in common terms the corresponding color. The description is based on three year old specimens of the new variety observed during September while grown outdoors on their own roots at Canet-des-Maures, Var, France.

Class: Shrub.

Plant:

*Height.*—Approximately 40 to 50 cm. on average.

*Diameter.*—Approximately 145 to 150 cm.

*Habit.*—Semi-prostrate.

Branches:

*Color.*—Young stems: light green, Yellow-Green Group 146B, more or less shaded with a reddish tint. Adult wood: bronzed green, Yellow-Green Group 146A.

Leaves:

*Stipules.*—Adnate, pectinate, narrow and linear.

*Petioles.*—Upper surface: grooved, reddish brown on young foliage and light green on adult foliage with more or less glandular edges. Under surface: light green with some thorns and glandular aciculas.

*Leaflets.*—Number: 3, 5 and 7. Shape: rounded. Serration: simple and regular. Texture: leathery. General appearance: dense foliage with a glossy aspect. Color (young foliage): Upper surface: light green, Yellow-Green Group 146B, more or less edged with a reddish tint. Under surface: very light green, Yellow-Green Group 146D, edged with a reddish tint. Color (adult foliage): Upper surface: medium green, Yellow-Green Group 147B. Under surface: very light green, Yellow-Green Group 146D.

Inflorescence:

*Number of flowers.*—Approximately 3 to 15 flowers per stem.

*Peduncle.*—Straight, rigid, medium green more or less shaded with a reddish coloration, approximately 3 cm. in length on average.

*Sepals.*—Upper surface: tormentose, greenish in coloration. Under surface: light green, smooth, the outside sepals have small appendiculated edges.

*Buds.*—Shape: ovoid. Length: approximately 1.5 to 2 cm. on average. Size: average. Color when opening: Upper surface: light salmon pink, Orange Group 27C. Under surface: orient pink, Red Group 36B.

*Flower.*—Form: double, opens as a flat cup. Diameter: approximately 6 cm. on average. Color (when opening begins): Upper surface: very pale orient pink, Red Group 36D. Under surface: pale orient pink, Red Group 36C. Color (when blooming): Upper surface: very pale orient pink, Red Group 36D. Under surface: pale orient pink, Red Group 36C. Color (at end of opening): Upper surface: very pale salmon pink, Orange Group 27D. Under surface: very pale orient pink, Red Group 36D. Fragrance: none. Lasting quality: long. Petal form: oval. Texture: firm. Petal number: approximately 28 to 32 on average. Petal drop: good. Stamen number: approximately 39 on average. Anthers: normal and bright yellow in coloration. Filaments: bright yellow and of irregular heights. Pistils: approximately 28 to 30 on average. Stigmas: greenish in coloration, located beyond the stamens, sometimes they are joined. Styles: more or less twisted, greenish in coloration, irregular in height. Receptacle: light green at the dehiscence of the anthers and in longitudinal section it is narrow and funnel shaped.

Development:

*Vegetation.*—Very vigorous.

*Blooming.*—Abundant and continuous.

*Aptitude to bear fruits.*—Good.

*Resistance to frost.*—Good.

*Resistance to diseases.*—Very good.

I claim:

1. A new and distinct variety of shrub rose plant characterized by the following combination of characteristics:

(a) forms attractive double blossoms which are very pale orient pink in coloration,
(b) forms petals which are firm and drop off cleanly,
(c) forms attractive flossy foliage,
(d) exhibits a semi-prostrate growth habit,
(e) exhibits good disease resistance, and
(f) is particularly well-suited for growing in the landscape;

substantially as herein shown and described, together with the parts thereof.

* * * * *